United States Patent [19]
Alam

[11] Patent Number: 5,942,187
[45] Date of Patent: Aug. 24, 1999

[54] PROTEIN ASSAY KIT

[76] Inventor: Aftab Alam, 32 Colwyn Road, Leeds, United Kingdom, LS11 6LQ

[21] Appl. No.: 08/048,940

[22] Filed: Apr. 20, 1993

Related U.S. Application Data

[63] Continuation of application No. 07/804,666, Dec. 10, 1991, abandoned.

[30] Foreign Application Priority Data

Dec. 11, 1990 [GB] United Kingdom ............... 9026822

[51] Int. Cl.$^6$ ..................................................... G01N 33/00
[52] U.S. Cl. ................................ 422/61; 436/86; 436/87; 436/88
[58] Field of Search .................................. 422/61; 436/86, 436/88, 87

[56] References Cited

U.S. PATENT DOCUMENTS

| | | | |
|---|---|---|---|
| 4,023,933 | 5/1977 | Bradford et al. | 436/88 |
| 4,104,030 | 8/1978 | Hopkins, II et al. | 435/18 |
| 4,239,495 | 12/1980 | Gindler et al. | 436/86 |
| 4,786,605 | 11/1988 | Mauck et al. | 436/86 |
| 5,077,222 | 12/1991 | Lau | 436/86 |

OTHER PUBLICATIONS

SU A 1167501 (STI) WPI Acc. No. 86–034413/05 Anal. Biochem. 186, pp. 285–287 (1990).
Anal. Biochem. 157, pp. 28–31, (1986).
Anal. Biochem. 150, pp. 278–287, (1985).
Anal. Biochem. 87, pp. 206–210 (1978).
Anal Biochem. 76, pp. 524–529 (1976).

*Primary Examiner*—Lien Tran

[57] ABSTRACT

The invention provides a kit for use in assaying protein, which comprises:

an alkaline copper solution containing a tartrate; and
    a solution of Folin reagent.

An alkaline copper solution containing tartrate has surprisingly been found to remain stable for several months. This allows a kit to be provided for use in a method of protein assay, in which the alkaline copper solution is provided ready-made up for immediate use in the method.

16 Claims, 12 Drawing Sheets

PROTEIN ASSAY KIT

This is a continuation of application Ser. No. 07/804,666, filed Dec. 10, 1991, now abandoned.

FIELD OF THE INVENTION

This invention relates to a kit for use in assaying protein.

BACKGROUND TO THE INVENTION

There are several methods for the determination of protein quantity in samples. These include the use of colour-changing dyes, such as Orange G, Bromo cresol green, Pyrocatechol Violet-Molybdenum complex, etc. These dyes, when bound with protein, change colour proportional to the amount of protein present in the samples. Such assay methods are generally not very sensitive. A more sensitive dye-binding technique using Coomassie Brilliant Blue G-200 is adversely affected by the presence of detergents in a sample and also suffers from wide protein-to-protein variation (Bradford, M., Anal. Biochem., 72 248–254, 1976 and U.S. Pat. No. 4,023,933).

A variety of turbidimetric methods are also known in which protein is precipitated by various agents. These methods also suffer from lack of sensitivity and specificity and interference with detergents.

The most widely used procedure for protein determination involves the well-known reaction of protein in alkaline medium with cupric ions yielding highly reactive cuprous ions. A method using alkaline copper was first developed by Lowry et al (Lowry, Oh. H., Rosebrough, N. J., Farr, A. L., and Randall, R. J., J. Biol. Chem. 193, 265–275, 1951) ("the Lowry method") in which protein reacted with buffered alkaline copper was coupled with Folin phenol reagent (phosphomolybdic/phosphotungstic acid), hereinafter referred to as Folin. It is believed that protein reacts with alkaline copper and produces cuprous ions and this, in turn, reduces the Folin to the characteristic blue reaction colour.

The Lowry method suffers from many disadvantages. The most serious disadvantage is the rigidity of the method. The Lowry method requires precisely-timed additions of reagent, immediate vortexing and prolonged incubation. Furthermore, the Lowry method also suffers from poor reproducibility and interference from a number of commonly used laboratory agents. Attempts to simplify the Lowry method have not, so far, been successful. Consequently, a need exists for a more flexible and rapid method for determination of protein.

In a recent modification, Smith et al (Anal. Biochem. 150, 76–85, 1985) combined the reaction of protein with alkaline copper with bicinchoninic acid. Although Smith et al's method has several advantages over the Lowry method, it suffers from lack of end-point in the reaction. The colour yield of the reaction continues to increase at a rate of 2–3% every ten minutes. Consequently, this method is not very accurate and the problem is compounded if a large number of samples are analysed in a single batch. In addition, Smith et al's method, using bicinchoninic acid, is a slow reaction requiring heating and a prolonged incubation period, which makes the method time-consuming.

STATEMENT OF THE INVENTION

According to the present invention there is provided a kit for use in assaying protein, the kit comprising:

an alkaline copper solution containing a tartrate; and
a solution of Folin reagent.

It has now been surprisingly discovered that unbuffered alkaline copper solution containing tartrate may be stored for several months without significant precipitation or deterioration. This is directly contrary to previous thinking, which has always held that an alkaline copper solution has an extremely short shelf life. The instability of such a solution has meant that it has always had to be prepared in situ, immediately prior to use, by combining a copper solution with an alkaline solution.

Thus, kits for performing protein assays which involve the use of an alkaline copper solution have always in the past comprised three separate components, ie an alkaline solution, a copper solution and a Folin solution. It has never before been thought possible to provide a ready-made-up alkaline copper solution for use in a method of protein assay.

It is thought that the presence of the tartrate increases the stability of the alkaline copper solution. The tartrate is preferably either sodium or potassium tartrate.

Preferably, the concentration of alkali in the alkaline copper solution is at least 0.2N, more preferably from 0.2 to 2N, and most preferably from 0.4 to 1N.

Such a kit could be used, for instance, in a method of assaying protein which comprises the following steps:

(a) contacting together a protein-containing solution and the alkaline copper solution of the kit;

(b) contacting together the product of step (a) above and the solution of Folin reagent, the amount of the Folin reagent preferably being such that the initial pH of the resultant solution is from 11 to 12; and (c) allowing the products of step (b) above to incubate at ambient temperature until the optical density of the solution reaches a maximum value and reading this maximum optical density in order to determine the amount of protein in the protein-containing solution.

Such a method is a two-step procedure in which no incubation period is required after the performance of the first step. As far as the second step is concerned, maximum optical density may be reached in as little as 10 minutes and this maximum optical density may be maintained over a period of, for instance, 10 to 40 minutes during which the optical density measurement may be taken. In the Lowry method, it is necessary to incubate for at least 10 minutes the products of the first step of the method and then wait for at least 30 or 40 minutes before making the optical density measurement after the second step of the method.

It had previously been considered that the second step of the Lowry method had to be carried out at a pH of about 10 and that the reaction solution should be maintained at this pH rather than being allowed to move downwardly, which would otherwise happen as the reaction proceeds and promotes decomposition of the coloured material in the solution. Contrary to accepted practice for very many years, it has now been discovered that a quite different approach to the pH of the reaction solution enables highly reproducible results to be obtained much more quickly than with the traditional Lowry method. The key to the discovery is that, in step (b) of the method, relatively very rapid reaction takes place at a pH of between 11 and 12, preferably between 11.4 and 11.9, more preferably between 11.5 and 11.8 and most preferably between 11.6 and 11.8. At the same time, the pH may be allowed to move downwardly rather than being maintained at this relatively high level. Movement of the pH downwardly means that the coloured species produced are relatively stable. Accordingly, a maximum optical density can be reached rapidly and held at the maximum level for a considerable period, more than sufficient to allow optical density measurements to be taken.

A relatively high alkaline concentration is preferably used in the kit of the invention, and hence in Step (a) of the above reaction. This has the added advantage that Step (a) of the reaction proceeds much more quickly than the first step of the conventional Lowry method. As a result, the normal incubation period which is required with the traditional Lowry method is not necessary in the practice of the method of the present invention. The Step (a) reactants may be mixed together and then immediately the Folin reagent may be added to enable the Step (b) reaction to proceed. The amount of alkali to be used has been defined above in terms of the concentration of alkali in the copper-containing solution. Although, in Step (a) of the method, the copper-containing solution is diluted by mixing with the protein-containing solution, in practice this does not result in a significant dilution of the alkali since the volume of protein-containing solution is normally no more than about one fifth, and often considerably less, than that of the copper containing solution.

It should be appreciated that the use of a relatively large amount of alkali in Step (a) of a method of protein assay (as when using the kit of the present invention) means that a correspondingly high relative amount of Folin reagent is used in Step (b). This ensures that most of the cuprous ions released as a result of the reaction between the copper (cupric) containing solution and the protein are immediately completed or otherwise reacted with the Folin reagent. It is believed that initially a colourless product is produced which rearranges to form the coloured species.

Sodium dodecyl sulphate (SDS) may be used in a protein assay method in order to counter the influence of nonionic and cationic detergents on the assay. For instance, the protein solution may be treated with SDS prior to the addition of Folin. Thus, the kit of the invention may additionally comprise a solution of sodium dodecyl sulphate. Alternatively, the alkaline copper solution may contain SDS.

The solution of Folin reagent in the kit is preferably in diluted form commercially available Folin phenol reagent is usually 2N. In the kit, the Folin is preferably in the form of Folin (2N) diluted 4–40 fold (0.5N—0.05N or 25%—2.5% Folin solution), more preferably in the form of Folin (2N) diluted around 20 fold (0.1N or 5% Folin solution). It has been found that such diluted Folin is usable for 6–12 months and longer. Therefore, it may be recommended to have a usable shelf life of 6–12 months or longer.

It has been found that such a diluted Folin solution, preferably diluted around 20 fold, overcomes interference by detergents such as Triton-X100, Tween-20, Bri-35 and others when used in protein assay methods. Thus, when used in the kit of the present invention, it can eliminate the need to include SDS in the alkaline copper solution in order to overcome interference by some detergents.

The kit of the invention is preferably provided with instructions for performing a method of protein assay using the kit. These instructions preferably relate to a method as described above. The reagents are preferably provided in containers of polymerised hydrocarbon, eg in polypropylene containers. The Folin is preferably supplied in a diluted ready-for-use form.

BRIEF DESCRIPTION OF THE DRAWINGS

A more complete appreciation of the present invention and many of its attendant advantages will be readily attained as the same becomes better understood by reference to the following detailed description and accompanying drawings, in which.

DETAILED DESCRIPTION

Figure 1:
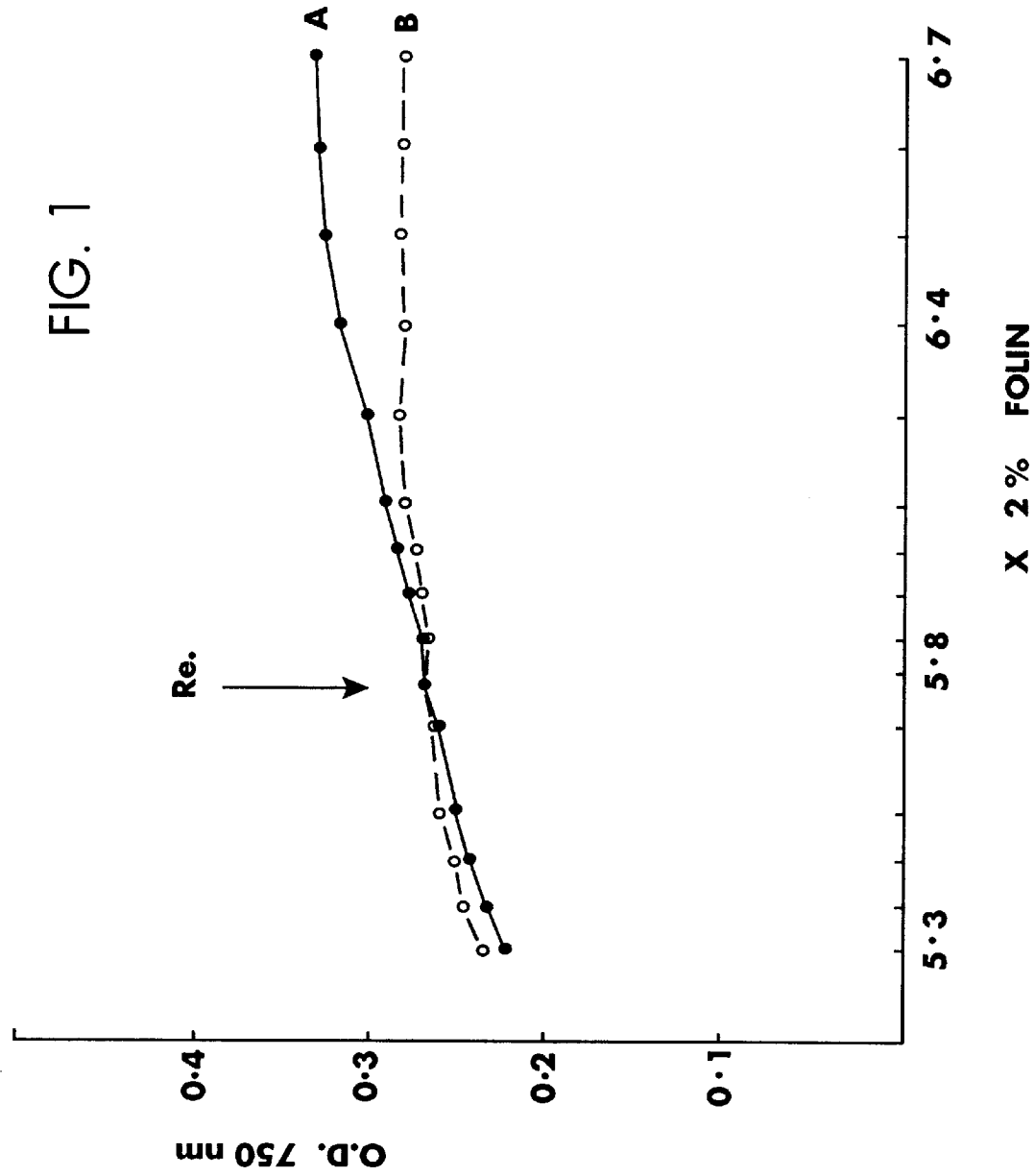
FIGS. 1 to 12 are graphs illustrating various aspects of a protein assay method carried out using a kit in accordance with the invention.

A typical protein estimation method based on the use of Folin reagent has two constituent reagent solutions, the first of which consists of copper in a solution of sodium hydroxide (alkali) and sodium or potassium tartrate, possibly buffered with sodium carbonate (hereinafter referred to as buffered alkaline copper solution), and the second of which is a solution of Folin phenol reagent. These reagent solutions have in the past always been reported to have short shelf-lives and have therefore always been made fresh, immediately prior to use.

The preparation of the buffered alkaline copper solution involved making two separate solutions and mixing them just prior to use. The solutions were:

Reagent-A, containing 2% sodium carbonate in 0.1N sodium hydroxide; and

Reagent-B, containing 0.5% copper sulphate pentahydrate in 1% sodium or potassium tartrate.

Reagent-A has always been made fresh, since the solution tends to develop precipitate and solid residue in storage. Reagent-B is also typically made fresh by mixing equal volumes of 1% copper sulphate and 2% sodium or potassium tartrate solutions. The working buffered alkaline copper solution would typically be made by mixing 50 parts of Reagent-A and 1 part of Reagent-B.

However, it has now been discovered that unbuffered alkaline copper solution, i.e. alkaline copper solution without a sodium carbonate buffering agent, can be stored for several months without significant precipitation and deterioration, provided tartrate is present (see Example 11 below). It is therefore possible to prepare a long term storable alkaline copper solution by mixing an alkaline solution containing tartrate with a copper solution. SDS may also be added to the alkaline copper solution. Thus, a kit in accordance with the invention comprises a ready-made alkaline copper solution, which may be stored prior to use in a protein assay method.

The Folin phenol reagent has always in the past been made fresh from 2N concentrated Folin solution, any unused diluted solution being discarded. However, it has now been discovered that dilute Folin phenol reagent (ie between about 0.5 and 0.05N) can be stored for several months at room temperature. The kit of the invention preferably comprises just such a ready-diluted Folin solution. It is important for long-term storage that pure de-ionised water is used in the preparation of a dilute solution of Folin reagent, and that the diluted Folin solution is protected from light. The diluted Folin solution should be stored in a container made of a polymerised hydrocarbon, such as polypropylene.

For estimation of the amount of protein in a sample, the sample is first treated with alkaline copper solution. It is widely believed that cupric copper in an alkaline medium reacts with protein and forms a copper-protein complex which in turn releases cuprous ions.

It has been discovered that when protein is treated with an alkaline copper solution containing a high concentration of alkali, the reaction of copper is almost instantaneous and requires no incubation for the subsequent reaction steps. In the experiments described below, in which protein was treated with alkaline copper solution containing 0.4N and 1N sodium hydroxide, the reaction of alkaline copper with protein was almost instantaneous and required no incubation. Example 5 below clearly proves that the reaction of copper with protein was so rapid that in 15 seconds (the time it takes to vortex the mixture to achieve a uniform mixing of the reagents with protein), the reaction of alkaline copper with protein was complete, and the colour yield of the reaction was identical to the control test sample which was incubated for 20 minutes in alkaline copper.

Folin reagent is next introduced into the copper-treated protein solution, which results in a characteristic blue colour. Many methods using Folin reagent for the estimation of protein recommend the addition of an amount of Folin reagent into the copper-treated protein which would give a reaction mixture of approximately pH 10. The addition of Folin reagent is followed by at least a 30 minute incubation period. Reaction at pH 10 is recommended to give a maximum yield of reaction colour and a greater stability to reaction colour.

However, a protein assay reaction between pH 10 and 11 has several disadvantages:
  at pH 10, the reaction progresses slowly and takes a long period of incubation to reach its maximum value;
  30 minutes' incubation does not bring the reaction to its end-point; and
  the optical density of the reaction colour continues to increase for a long time after 30 minutes' incubation, at a rate of 5% to 25% per hour, depending on the starting pH of the reaction mixture. The increase in optical density contributes to error in the protein estimation.

Figure 3:
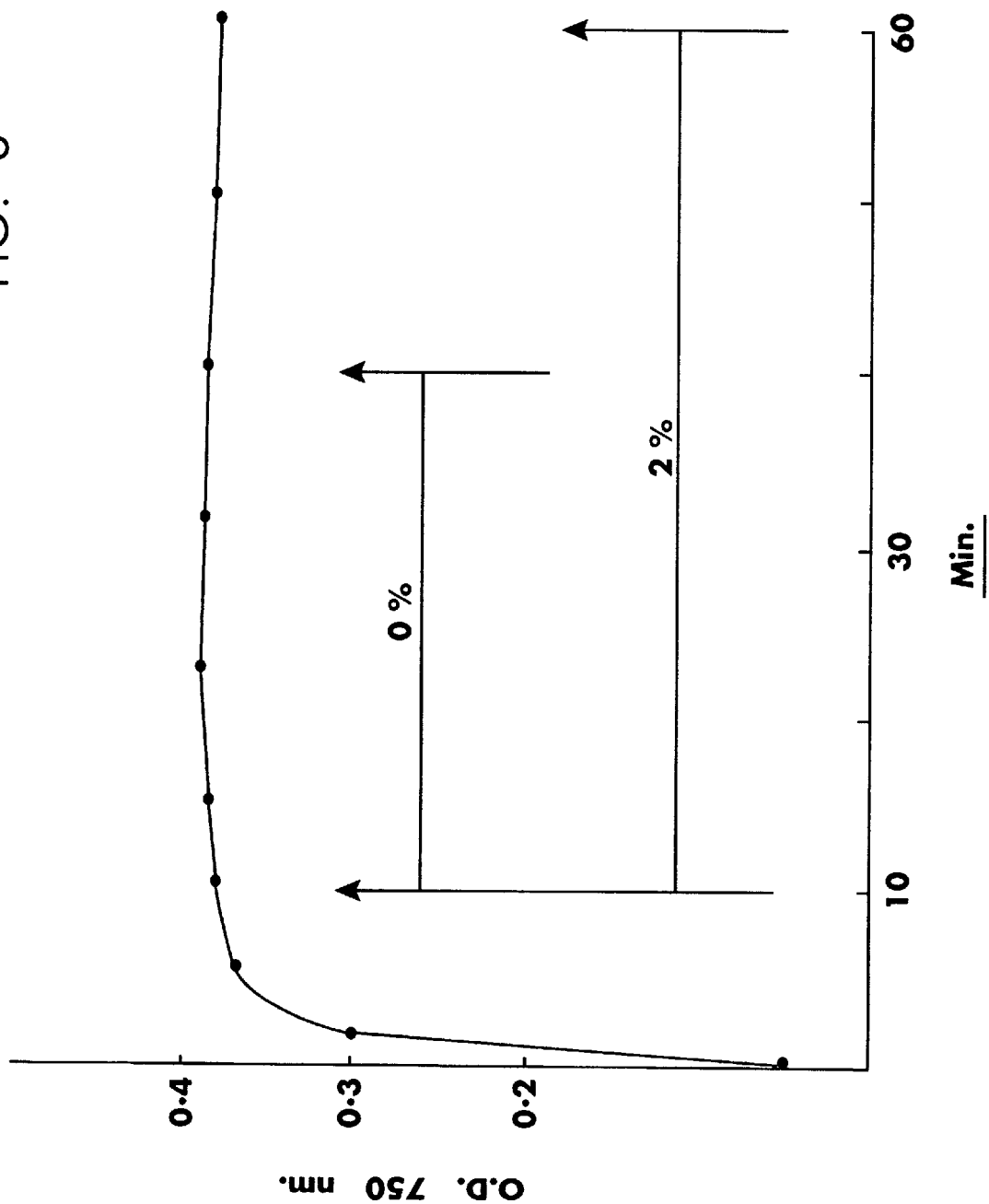
Figure 8:
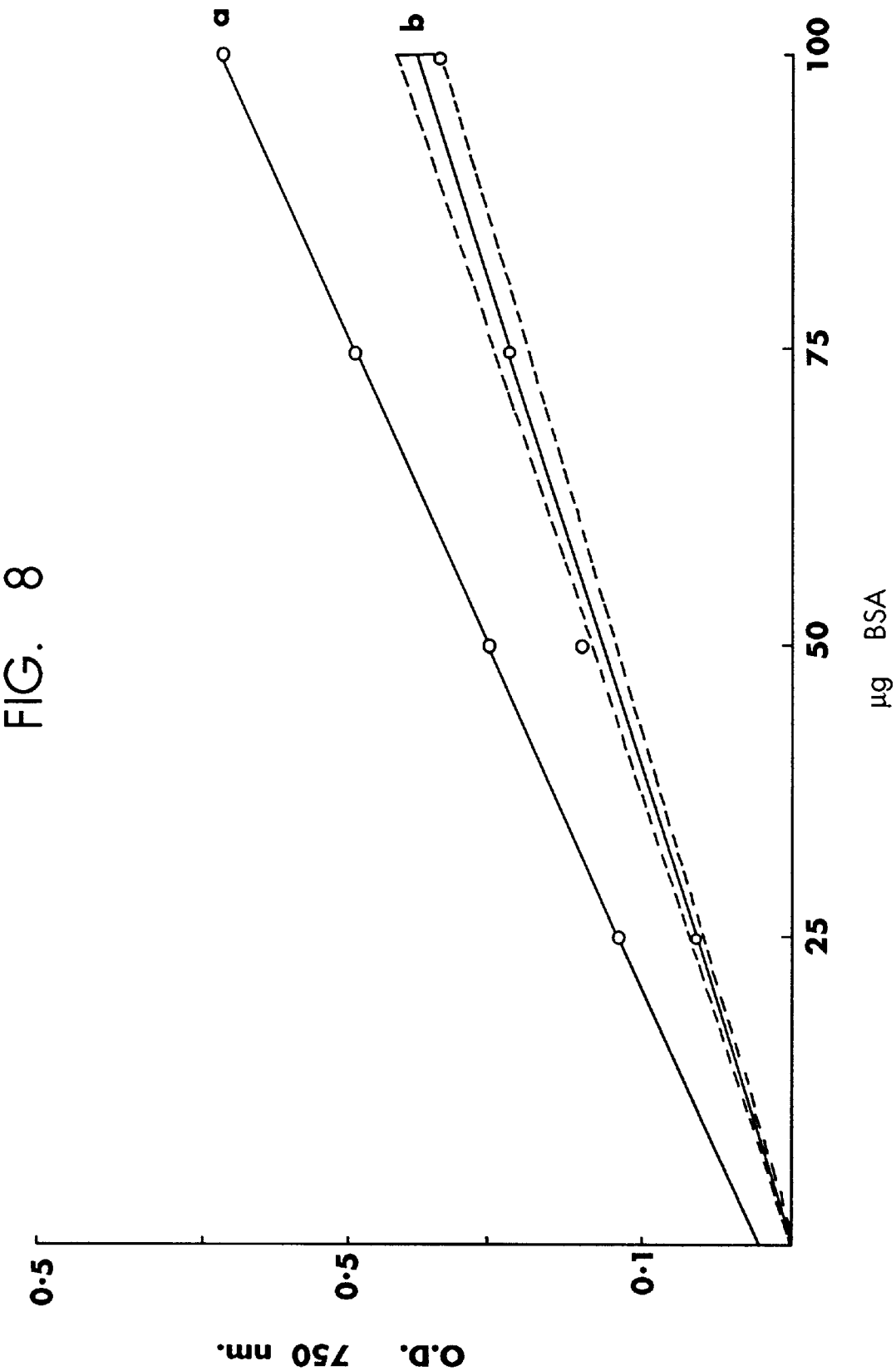

Protein estimation can, however, be performed more rapidly and with substantially increased sensitivity and reproducibility at high alkaline pH, i.e. between pH 11 and 12. It has also been found that the rapid release of reaction colour between pH 11 and 12 produces results which are more reproducible than slow release, as shown in FIG. 8. At pH 11–12 the reduction and colour development of Folin reagent with copper-treated protein reaches a maximum and an end-point more rapidly and, in addition, the reaction produces a plateau of stable optical density for the reaction. The higher the pH, the more rapidly colour development takes place. It has also been found that at the preferred pH of between 11.5 and 11.9, the colour development reaches a maximum and an end-point within 10 to 15 minutes, and stays nearly constant. This enables reliable determination of a large number of samples in a batch. It has also been found that after reaching the maximum, the decrease in optical density in one hour could be as little as 1% to 2% when measured in steady state, as shown in FIG. 3.

Thus, the components of a kit in accordance with the invention should ideally be reacted together in such relative proportions as to yield an initial pH, in the copper solution-protein mixture, of the order described above.

It has also been found possible to perform a protein assay within a pre-selected time by pre-selecting the reaction commencing pH of the assay mixture and reading the reaction colour at the plateau of the maximum optical density. The pre-selection of assay time is made possible by carefully selecting the amounts of alkaline copper solution and Folin solution which, on mixing, could result in a pH at which the reaction colour will reach the maximum and end-point within the pre-selected time. Tables 1, 2 and 3 in Example 3 give the reaction commencing pH required for various pre-selected times, and the length of time for which the optical density remains nearly constant.

It has been discovered that at the reaction commencing pH in buffered alkaline medium around pH 11.70, the reduction of Folin and colour development reaches maximum in around 10 minutes, and stays nearly constant for 15 to 20 minutes, which is sufficient to allow reading of 40–50 separate samples, and in 40 minutes after reaching the end-point maximum, the colour drift is within 3% to 4%. The optical density drift of 3% to 4% is comparable to the drift in the optical density reported for the widely used method of protein determination by Bradford, M. M. (Anal. Biochem. 1976, 72, 248–254), and considerably better than the 16% drift in the optical density of another widely used method by Smith, P. K. et al (Anal. Biochem., 1985, 150, 76–85). In addition, it has also been found that, in a real determination in accordance with the present invention, the expected drift was not detected, as is shown in Example 3.1 and FIG. 8.

A further improvement in the reaction is achieved when a kit containing an unbuffered alkaline copper solution is used for the assay. In unbuffered alkaline medium, the pH of the reaction drops unhindered and more rapidly, and in less than 10 minutes the pH drops as much as 0.15–0.6 units for a reaction commencing between pH 11 and 12 (Table 2, FIG. 3). This finding has two advantages:
  it allows a rapid release of reaction colour at a very high alkaline pH; and
  as soon as the maximum reaction colour is achieved and before substantial decomposition of colour can begin, the pH of the reaction also shifts to a pH at which the decomposition of the reaction colour is very considerably reduced (Tables 1 and 2, FIG. 3).

The reaction shown in FIG. 3, which could be carried out using a kit in accordance with the invention, commences at a pH around 11.70. In less than 10 minutes the release of colour reaches a maximum value and concurrently the pH of the reaction mixture drops by 0.2 units to pH 11.5. At pH 11.5, the optical density of reaction colour is virtually unchanged for over 30 minutes (Tables 1 and 2, FIG. 3) and in the next 30 minutes, the optical density drops by a mere 2% to 3%. The shift in optical density of 2% to 3% in the second half-hour of a one-hour period is less than the method of Bradford cited above.

In a further study, neither sodium carbonate nor sodium tartrate were present in the alkaline copper solution. The removal of tartrate from the alkaline copper solution (Example 3.3) lowered the rate of reduction of Folin with copper-treated protein and consequently it took longer for the reaction colour to reach a maximum value, and at maximum the reaction colour was generally more stable. The results in Table 3 show that a reaction commencing at pH 12 took approximately 10–12 minutes to reach the maximum as compared to 5 minutes in unbuffered and buffered alkaline solution (Tables 1 and 2). In addition, in the absence of tartrate, the reaction colour was more stable after reaching the maximum value, as shown in Table 3.

However, it has been found that tartrate improves the stability of an alkaline copper solution, whereas in the absence of tartrate copper tends to precipitate from the solution. The higher the concentration of tartrate in fact, the more stable the alkaline copper solution.

It has been discovered that when the tartrate concentration in an alkaline copper solution is around 0.1% or three times (×3) the concentration of copper, the alkaline copper solution is stable for months.

Preferably, the tartrate concentration in the alkaline copper solution should be over 0.2% or five times (×5) the concentration of copper. Most preferably, the concentration of tartrate should be over 0.5% or ten times (×10) the concentration of the copper (see Table 4).

When Folin is added to a copper-treated protein, maximum colour results if the reduction occurs at a pH around pH 10. The reduction of Folin at higher pH between pH 11–12 results in lowering of the yield of reaction colour and consequently reduces the sensitivity of an assay. It has been discovered that the colour yield of the reaction at higher alkaline pH could be increased to its maximum value or to a level which is comparable to the traditional methods based on the use of Folin reagent. The yield of reaction colour is maximised by increasing the amount of Folin in an assay, which is achieved by increasing the concentration of alkali in the alkaline copper solution used. Thus, the kit of the invention includes an alkaline copper solution having a relatively high concentration of alkali. Example 4 shows that as the concentration of alkali is increased in an alkaline copper solution, it requires correspondingly increased amounts of Folin to achieve a pH of around 11.7 and consequently the colour yield in an assay is increased to a much higher value than it would be possible to achieve at pH 10 in 10–15 minutes. Example 7 demonstrates the increased sensitivity of such a method, using a kit in accordance with the invention, over the Lowry method.

It has also been discovered that rapid release of reaction colour at a relatively higher alkaline pH, i.e. pH 11–12, results in improved reproducibility of protein estimation. Plot A of Example 6 shows a typical estimation of protein using an assay kit as described in this invention, using a relatively high pH. The points in the plot make a perfect straight line, leaving no room for ambiguity. Plot B on the other hand is based on the determination at pH 10.5. The points on the plot are scattered and it is possible to draw more than one straight line through them.

When Folin is added to protein treated with alkaline copper, the reagent is only reactive for a short time, and it is for this reason that Folin is preferably added while vortexing the reaction mixture. It is difficult to achieve uniformity with a large number of samples in a batch while adding Folin to a vortexing mixture. It has been found that this problem can be eliminated by keeping the volume of copper-treated protein small and introducing Folin forcibly in a volume larger than the volume of copper-treated protein. The forcible addition of Folin creates instantaneous mixing of Folin with copper-treated protein which ensures uniform mixing of the reagents in a batch.

Protein assay methods based on the reduction of Folin by copper treated protein suffer from interference by a number of commonly used laboratory reagents, particularly nonionic and cationic detergents such as Triton-X100. This interference can be eliminated by introducing into the assay, prior to the addition of Folin, a small amount of an anionic detergent such as SDS. This is best achieved by the inclusion of SDS in the protein assay kit. Example 8 shows that addition of SDS in an assay eliminates interference by Triton-X100.

It has also been found that it is difficult to maintain SDS in a solution of sodium hydroxide having a concentration higher than 0.4N. SDS in as low a concentration as 0.5% has a tendency to precipitate on standing in sodium hydroxide solution of concentration higher than 0.4N. It is therefore preferred that SDS is provided as a separate component in an assay kit, and kept separate from the alkaline copper solution, the two solutions being mixed prior to use. The SDS solution may be warmed prior to use to maintain the SDS in solution.

SDS can be dissolved either with tartrate or copper sulphate and stored for a long time. SDS can also, although this is not preferred, be included in an alkaline copper solution and stored for several months (see Example 11).

EXAMPLES

The examples set out below were used to investigate the characteristics of a protein assay method, which could be carried out using a kit in accordance with the invention. Also investigated were the properties of the components of such a kit, of relevance to the preferred characteristics of the kit for use in a protein assay.

Example 11 particularly investigates the stability of an alkaline copper solution, for use as one of the components of the kit.

The materials and methods used in the examples were as follows:

Reagents

Copper sulphate pentahydrate, potassium tartrate, sodium tartrate, sodium carbonate, sodium hydroxide, sodium dodecyl sulphate (SDS) and bovine serum albumin (BSA) were obtained from Sigma Chemical Co. The alkaline copper solution was made in two parts, the first part (hereinafter referred to as "the alkaline solution") of which contained sodium hydroxide, sodium carbonate, sodium or potassium tartrate and SDS. The second part was a concentrated solution of copper sulphate. The Folin reagent solution was made using a 2N Folin reagent starting solution.

Reagent Preparation

Various concentrations of alkaline solution were prepared. They were 0.4N, 0.8N, 1N and 2N sodium hydroxide solution. Either 4% or 5% sodium carbonate and 0.16% sodium tartrate were added to the alkaline solution. Similarly, SDS was added to the alkaline solution to a final concentration of 0.5% to 2%. The alkaline solution was stored at room temperature in polypropylene bottles. A 5% copper sulphate solution was made in distilled water and stored at room temperature in a polypropylene bottle. The working alkaline copper solution was made by mixing 10 ml of alkaline solution with 0.1 ml of 5% copper sulphate solution.

Folin solutions were made using pure de-ionised water. 2%, 5% and 10% Folin solutions were made using a 2N Folin solution and stored at room temperature in polypropylene bottles protected from light. Bovine serum albumin (BSA) was dissolved in distilled water to a final concentration of 2 mg/ml and used as standard stock.

Protein Assay Method

Protein solutions containing 10 to 200 $\mu$g protein in a volume of 0.05 to 0.2 ml were pipetted into test tubes. The alkaline copper solution was added to the test tubes in a volume equal to 1–5 times the volume of protein solution in the test tubes, and vortexed. Immediately after vortexing, unless otherwise specified, an appropriate volume of Folin reagent solution was forcibly introduced into the test tubes. The test tubes were incubated for 10 minutes at room temperature and absorbency at 650–750 nm was measured. The weight of protein was plotted against the corresponding absorbence, resulting in a standard calibration curve used to determine the amount of protein in unknown samples.

Micro Protein Assay

Protein solutions containing 1 to 8 ug protein in a volume of 5 ul were pipetted into either micro test tubes or microtiter plates. Alkaline copper solution was added into the micro test tubes in a volume equal to 4–5 times the volume of protein solution, i.e. 20–25 ul. An appropriate volume of Folin reagent solution was forcibly introduced into the micro test tubes. The micro test tubes or microtiter plates were incubated at room temperature for 10 minutes and then absorbences at 650–750 nm were read. The weight of protein was plotted against the corresponding absorbence, resulting in a standard calibration curve used to determine the amount of protein in unknown samples.

Example 1

Determination of Short Incubation Period for Protein Assay

A series of duplicate samples of standard protein solution containing 0.2 mg protein in a volume of 0.1 ml were treated with 0.5 ml of alkaline copper solution containing 0.4N NaOH in 4% sodium carbonate, 0.16% sodium tartrate and 0.05% copper sulphate. After mixing, the contents were treated with increasing volumes of 2% Folin reagent, introduced forcibly. The volume of 2% Folin was increased from 5.2 times the total volume of copper-treated protein (i.e. 0.6 ml) to 6.7 times. The optical density was read after 10 minutes (Plot B) and after 30 minutes (Plot A) incubation at room temperature. The results gave the-plots shown in FIG. 1. As seen from the graph, the optical density taken after 30 minutes' incubation (Plot A) crosses over the optical density taken after 10 minutes' incubation (Plot B). The crossover point is referred to in the graph as "Re" and marked with an arrow. The crossover point has a reaction commencing pH of around pH 11.70. It is clear from the graph that the reduction of Folin with copper-treated protein at pH around pH 11.7 reached its end-point maximum in around 10 minutes, and the optical density remained unchanged for the next 20 minutes. The reduction of Folin at a pH significantly higher than pH 11.70 begins to decline rapidly after 10 minutes and, similarly, the reduction of Folin at a pH significantly lower than pH 11.70 continues to increase after 10 minutes' incubation. It is clear from these graphs that a protein assay method based on the reduction of Folin at a pH around pH 11.70 can be developed which will reduce the incubation period to around 10 minutes. At a pH of around 11.70 the optical density stays nearly constant for long enough to allow assay of a large number of samples without significant drift in determination.

Example 2

Determination of Stability of Reaction Colour

Figure 2:
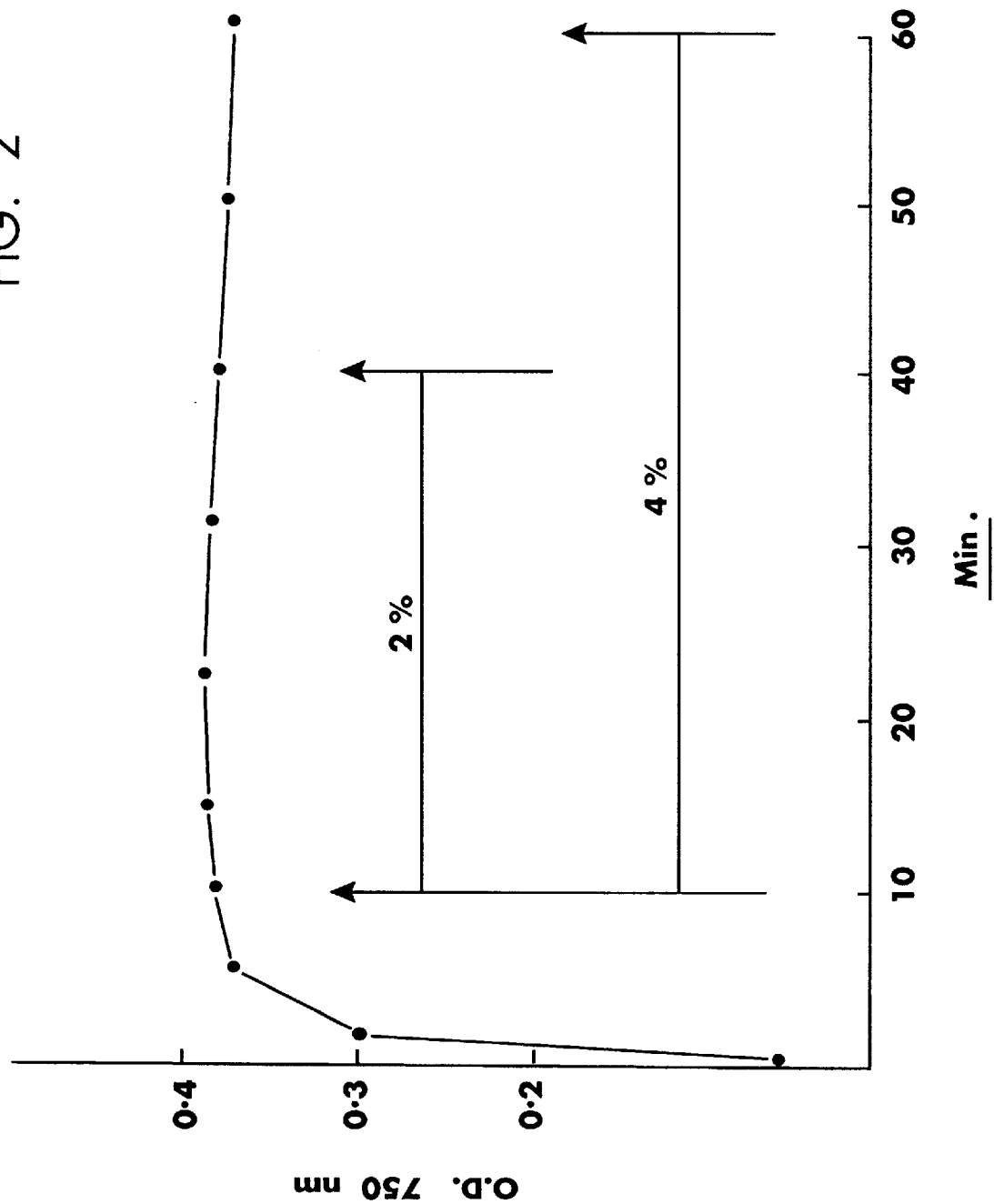

A sample of standard protein solution containing 0.1 mg protein in 0.1 ml was mixed with 0.5 ml of alkaline copper solution containing 1N NaOH in 5% sodium carbonate, 0.16% sodium tartrate and 0.05% copper sulphate. After mixing, 3.55 ml of 5% Folin reagent was forcibly introduced. A 1 ml portion was removed for pH determination, and the remainder was used to measure the optical density. The optical density was continuously measured for one hour. The pH at the commencement of the reaction was measured within 1.5 minutes, and was approximately pH 11.70. The optical density result gave the plot shown in FIG. 2. It is clear from the graph that the reduction of Folin commencing at a pH around pH 11.70 caused rapidly increased optical density and reached its end-point maximum in around 10 minutes, which changed very little for the next 50 minutes. It was estimated that, after reaching the end-point maximum in 10 minutes and for the next 15–20 minutes, the decline in optical density was negligible (around 1%) and in the subsequent 20–25 minutes, it was around 3%–4%. An overall drift in the optical density of 3%–4% in one hour is comparable to the widely used method by Bradford, M. M. (Anal. Biochem. 1976, 72, 248–254) and considerably better than the 16% drift in the optical density of another popular method by Smith, P. K. (Anal. Biochem., 1985, 150, 76–85). The results also show that in a 45-minute period, the pH of the reaction gradually drops by approximately 0.2 units.

In a similar experiment to that described above, the protein was treated with unbuffered alkaline copper solution containing 0.16% sodium tartrate and 0.05% copper sulphate in 1N NaOH. After mixing, 3.7 ml of 5% Folin reagent was forcibly introduced and the reaction pH was read within 1.5 minutes of mixing: this was around pH 11.70. The optical density gave the plot shown in FIG. 3. The result shows rapid reduction of Folin, which reached a maximum within 10 minutes. The optical density remained virtually unchanged for over 30 minutes and, after that, it began to decline gradually. In a 60-minute period, the drift in reaction colour was around 2%–3%, which is a considerable improvement on the example described above. The result also shows that the pH drops by approximately 0.2 units in the first 10 minutes, and approximately 0.3 units in 30 minutes, of the reaction.

Example 3.1

Stability of Optical Density at Various Reaction pHs in Buffered Medium

A sample of standard protein solution containing 0.1 mg protein in 0.1 ml was mixed with 0.5 ml of buffered alkaline copper solution containing 1N NaOH in 5% sodium carbonate, 0.16% sodium tartrate and 0.05% copper sulphate. The copper-treated protein solution was treated with increasing amounts of 5% Folin (3.1 ml to 4.6. ml). The optical density of reaction colour was recorded and the pH of the reaction was recorded at intervals. The results were tabulated as shown in Table 1.

TABLE 1

| Volume of 5% Folin (ml) | Approximate Reaction pH 0   45 (Minutes) | Approximate Time to Reach Maximum (Minutes) | Approximate Length of Plateau at Maximum (Minutes) |
| --- | --- | --- | --- |
| 3.1 | 12.10–11.95 | 4–5 | 4–5 |
| 3.2 | 12.00–11.88 | 5–6 | 6–8 |
| 3.3 | 11.95–11.75 | 6–7 | 8–9 |
| 3.4 | 11.85–11.62 | 6–8 | 10–12 |
| 3.5 | 11.75–11.58 | 8–10 | 20–22 |
| 3.6 | 11.65–11.40 | 10–12 | 25–30 |
| 3.7 | 11.55–11.30 | 13–14 | 40–45 |
| 3.8 | 11.53–11.30 | 15–17 | >50 |
| 3.9 | 11.40–11.12 | 16–18 | >60 |
| 4.1 | 11.23–11.95 | 18–20 | >60 |
| 4.3 | 11.10– | 32–34 | >60 |

It is clear from the Table above that the reduction of Folin with copper-treated protein commencing at a pH of between 11.8 and 11.60 reached its end-point maximum in around 8–10 minutes. After reaching its maximum, and for the next 15–20 minutes, the optical density remained nearly constant. The deviation in optical density in a 30-minute period was negligible at around 1%. The deviation in the subsequent 30 minutes was around 3%–4% (not shown in Table 1). The reduction of Folin commencing at a pH of between 11.60 and 11.40 reached its maximum in around 15–20 minutes and stayed nearly constant for 30–40 minutes. In the subsequent 30 minutes, the decline in optical density was around 3% to 4%.

It is clear from Table 1 that the higher the alkalinity of the reaction, the more rapidly production of reaction colour takes place and, conversely, the higher the alkalinity, the shorter is the length of the plateau at the maximum optical density. At the reaction pH 11.75, a reasonable balance is struck and the reaction takes under 10 minutes to reach its maximum colour, while the plateau at the maximum lasts around 15–20 minutes. The reaction commencing at pH 11.50 would take around 20 minutes to reach the maximum colour, and the colour at the maximum would remain unchanged for over 30 minutes. Lowering the alkalinity substantially increases the time it takes to reach the maximum reaction colour, although it also increases the stability of the reaction colour. It has also been found that the rate of decomposition of the reaction colour is considerably reduced by lowering the alkalinity (not shown in this table). The reaction colour is stable for over 30 minutes when the pH at the plateau is lowered to around pH 11.50 and beyond. It is also clear from Table 1 that, in buffered alkaline medium, during the course of reaction the pH of the reaction mixture gradually decreases, and in 45 minutes the pH decreases by approximately 0.2 units.

Example 3.2

Stability of Optical Density at Various Reaction pHs in Unbuffered Medium

A sample of standard protein solution containing 0.1 mg protein-in 0.1 ml was mixed with 0.5 ml of unbuffered alkaline solution of copper, containing 1N NaOH in 0.16% sodium tartrate and 0.05% copper sulphate. The copper-treated protein was treated with increasing amounts of 5% Folin (3.4–4.0 ml). The optical density of the reaction colour was recorded, and the pH of the reaction was recorded at intervals. The results were recorded in Table 2 and FIG. 3.

TABLE 2

| Volume 5% Folin (ml) | Approx. Reaction pH 0   15   45 (Minutes) | Approx. Time to Reaction Maximum (Minutes) | Approx. Length of Plateau at Maximum (Minutes) |
|---|---|---|---|
| 3.4 | 11.95–11.77–11.65 | 5–6 | 10–11 |
| 3.5 | 11.87–11.70–11.58 | 8–9 | 18–20 |
| 3.6 | 11.80–11.60–11.50 | 9–10 | 24–26 |
| 3.7 | 11.75–11.58–11.48 | 9–10 | 26–28 |
| 3.75 | 11.73–11.53–11.45 | 10–11 | 28–30 |
| 3.8 | 11.65–11.49–11.33 | 16–18 | 50–55 |
| 4.0 | 11.55–11.33–11.20 | 30–35 | >75 |

It is clear from the results that in unbuffered alkaline medium, the pH of the reaction mixture drops more rapidly than in the buffered medium (Table 1), and a drop of approximately pH 0.2 units takes place in under 10 minutes. Consequently, when the reaction is commenced at around pH 11.70, it rapidly releases the reaction colour and reaches a maximum in around 10 minutes. The reaction releases acid and as a result, the pH drops to around pH 11.50 which happens to be a pH at which the reaction is nearly unchanged for well over 30 minutes (Table 1).

The overall effect is a rapid release of reaction colour at a very high alkaline medium (in around 10 minutes) and, as the maximum reaction colour is reached, the pH of the reaction drops to a pH at which the decomposition of the colour in 60 minutes is insignificant. It has been found that in a 60-minute period the drift in optical density is around 2%.

Example 3.3

Rate of Folin Reduction and Stability of Reaction Colour in the absence of Tartrate in Unbuffered Alkaline Copper Solution The experiments were performed as described in Example 3.2, except that tartrate was not added in the alkaline copper solution. The results, shown in Table 3, show that in the absence of tartrate the reduction of Folin by copper-treated protein proceeds slowly.

TABLE 3

| Volume 5% Folin (ml) | Approx. Reaction. pH 0   15   45 (Minutes) | Approx. Time to Reaction Maximum (Minutes) | Approx. Length of Plateau at Maximum (Minutes) |
|---|---|---|---|
| 3.4 | 11.95–11.75–11.61 | 10–12 | 24–25 |
| 3.6 | 11.78–11.60–11.49 | 14–16 | 28–30 |
| 3.7 | 11.68–11.48–11.33 | 17–18 | 60–65 |
| 3.8 | 11.65–11.40–11.30 | 25–27 | >65 |

The results in Table 3 show that the reaction commencing at pH 12 took approximately 10–12 minutes to reach the maximum as compared to 5 minutes in unbuffered and buffered alkaline solution as shown in Tables 1 and 2. In addition, in the absence of tartrate, the reaction colour was more stable after reaching the maximum value.

EXAMPLE 3.4

A Model for Protein Assay at High Alkaline pH

Figure 4:
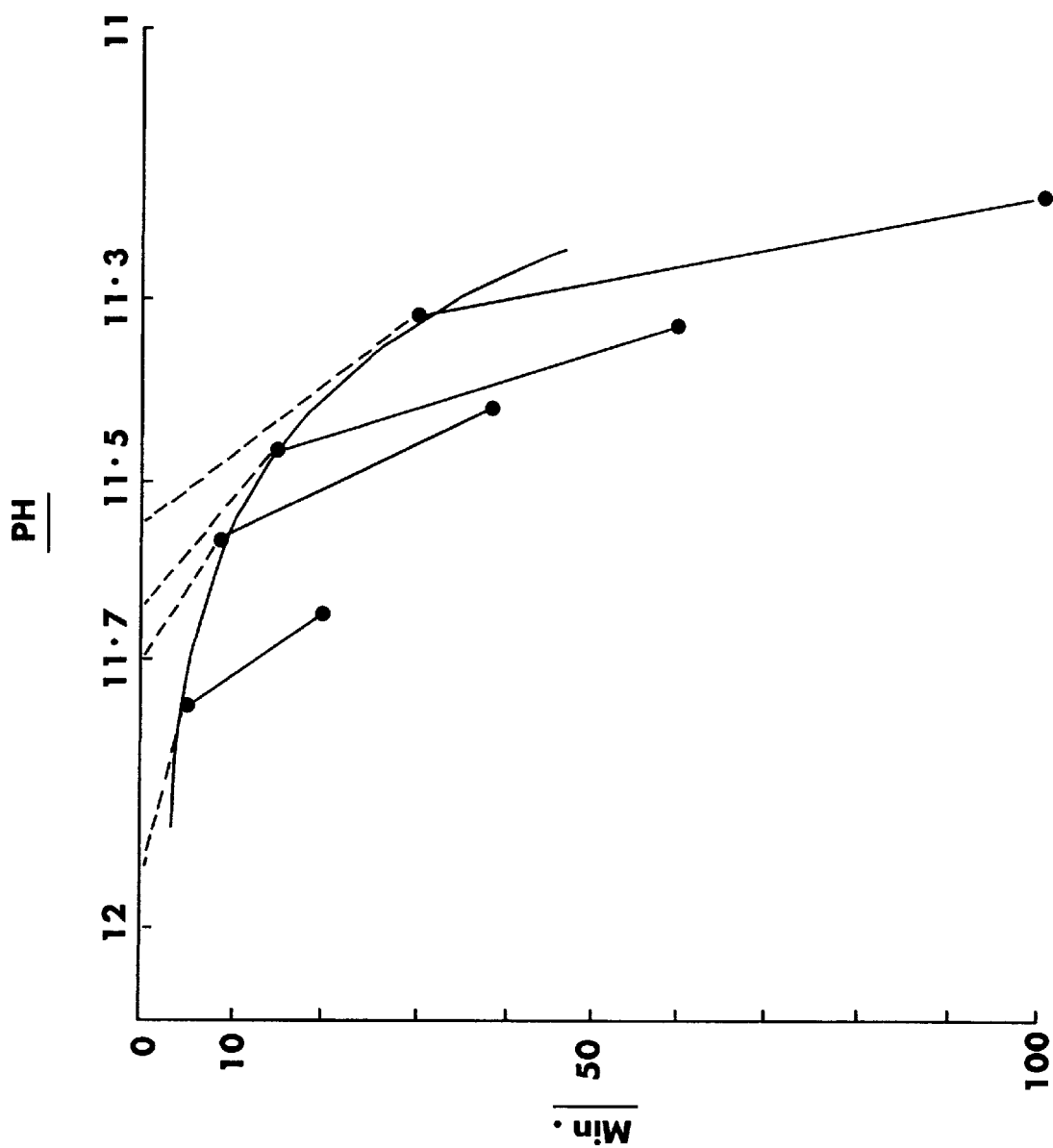

The results of Example 3.2 were plotted to create a model for protein assay at high alkaline pH. FIG. 4 shows the plot. Reaction commencing pH was plotted against time. The broken lines show the changes in the reaction pH before reaction colour optical density reached a maximum value. The semicircle represents the time, corresponding to reaction commencing pH, that it took a reaction to reach its maximum value. The solid lines show the length of time the optical density of reaction colour remained stable. It is clear from the model that the higher the alkalinity of the reaction, the more rapidly the release of reaction colour takes place. Conversely, the higher the alkalinity, the shorter is the length of stable optical density at maximum. When reduction of Folin commences at a pH around 11.7, it reaches the maximum reaction colour in approximately 10 minutes. Having reached the maximum value, the reaction colour optical density remains virtually unchanged for the next 30 minutes.

Example 4

Maximising the Release of Reaction Colour

Figure 5:
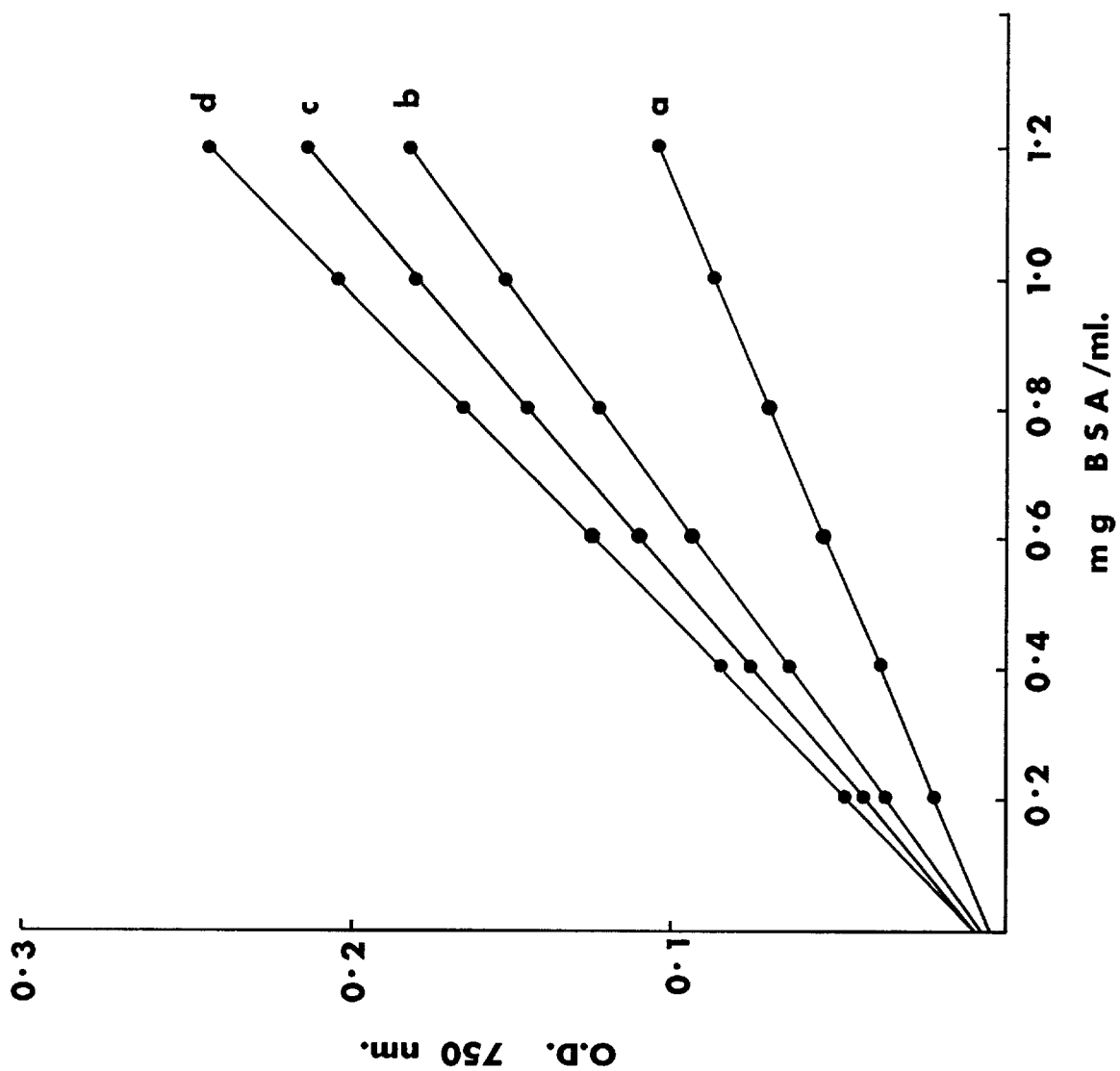

The experiment consisted of a batch of four determinations, a, b, c and d. Duplicate samples of 0.1 ml protein solution containing 0.2–1.2 mg/ml were pipetted for each batch. Batches a, b, c and d were treated with 0.1, 0.2, 0.3 and 0.4 ml alkaline copper solution (containing 0.4N NaOH in 4% sodium carbonate, 0.16% sodium tartrate and 0.05% copper sulphate). After mixing the contents, 1.16, 1.74, 2.32 and 2.9 ml of 2% Folin reagent was forcibly added to a, b, c and d respectively. After an incubation of 10 minutes, the optical density was read and the results gave the plots shown in FIG. 5.

The next experiment consisted of a batch of three determinations, a, b and c. Duplicate samples of 0.1 ml protein solution containing 0.2–1.2 mg/ml were pipetted for each batch. The protein solutions were treated with 0.5 ml alkaline copper solutions, the compositions of which were as follows:

1. 0.4N NaOH containing 4% sodium carbonate, 0.16% sodium tartrate and 0.05% copper sulphate;
2. 1N NaOH containing 5% sodium carbonate, 0.16% sodium tartrate and 0.05% copper sulphate;
3. 2N NaOH containing 5% sodium carbonate, 0.16% sodium tartrate and 0.05% copper sulphate.

Figure 6:
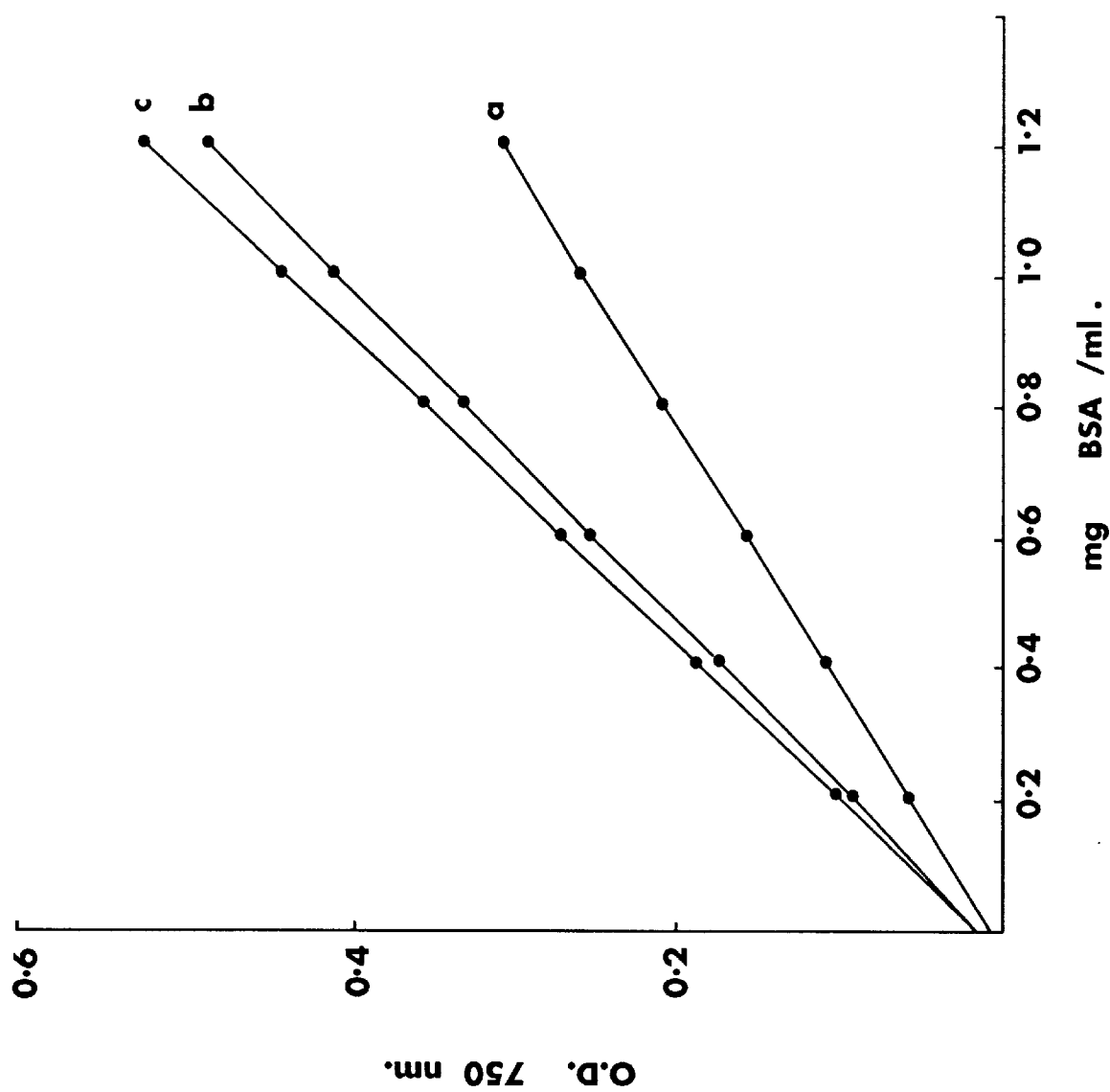

Batches a, b and c were treated with alkaline copper solutions 1, 2 and 3 respectively. After mixing the contents, batches a, b and c were treated with 3.5 ml of 2%, 5% and 10% Folin reagent respectively. The optical density was recorded and the results gave the plots shown in FIG. 6. It is clear from FIGS. 5 and 6 that the release of reaction colour can be increased and maximised by increasing either the amount or the concentration of alkali and correspondingly increasing the amount of Folin solution in the assay.

Example 5

Determination of Cu-Protein Complexing Time

Figure 7:
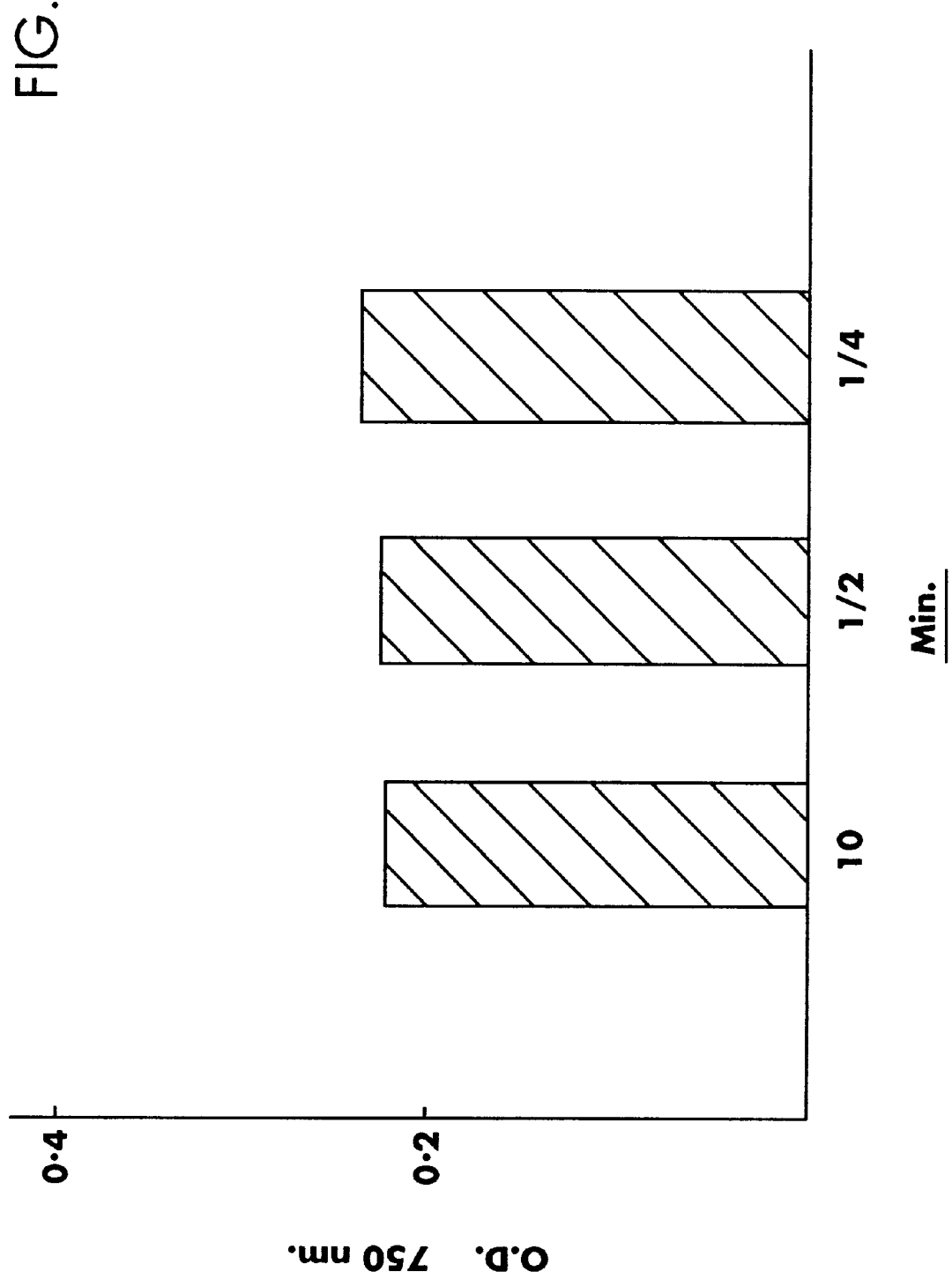

Triplicate protein solutions containing 0.1 mg of protein in 0.1 ml were mixed with 0.5 ml of alkaline copper solution containing 1N NaOH in 5% sodium carbonate, 0.16% sodium tartrate and 0.05% copper sulphate. The contents were mixed immediately and, without delay, 3.5 ml of 5% Folin solution was forcibly introduced. The whole procedure took around 15 seconds to complete. Three more samples were treated identically except that Folin solution was added after incubation periods of ½, 1 and 10 minutes. The optical density was read after 10 minutes and the results gave the histogram shown in FIG. 7. It is clear from the results that copper complexed with protein immediately after the addition and mixing. Similar results were obtained when protein was treated with alkaline copper solution containing 0.4N NaOH. It is clear that copper complexed with protein immediately in alkaline solution containing as little as 0.4N NaOH.

Example 6

Reproducibility and Accuracy of the Assay

Reproducibility and accuracy of the assay were examined by performing identical determinations. Samples containing 0.025–0.1 mg/ml were mixed with 0.5 ml of alkaline copper solution containing 1N NaOH in 5% sodium carbonate, 0.16% sodium tartrate and 0.05% copper sulphate. After vortexing the mixture, 3.5 ml of 5% Folin solution was forcibly introduced into the copper-treated protein solution. The pH of the reaction mixture was measured around 11.75. The optical density of the assay reached its maximum in around 10 minutes. The optical density was repeatedly read after 10 minutes, and the results gave Plot A shown in FIG. 8. An identical determination was also performed in which the reaction was commenced at pH 10.5, and the results gave Plot B shown in FIG. 7. The results show clearly that protein estimation based on the method described produces highly reproducible results. In Plot A, the points give a perfect straight line and, on the other hand, the estimation based on pH 10.5 of the reaction has a larger deviation (Plot B).

Figure 9:
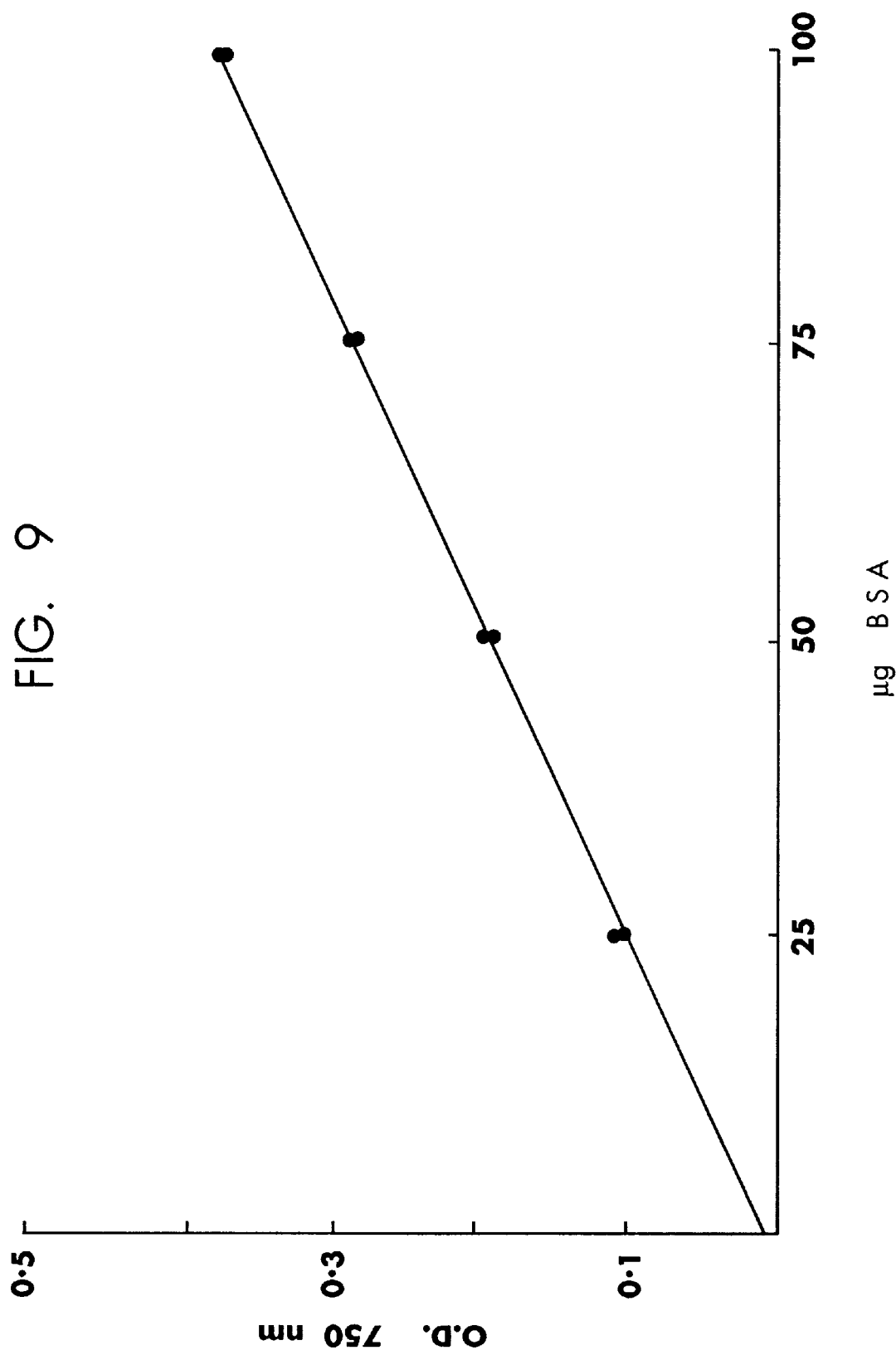

In a further extension of this experiment, the samples of Plot A were repeatedly read for an hour, and the results are shown in FIG. 9. The results show clearly that in a one-hour measurement, the expected drift in the optical density was not detected, and the points were closely packed. The inclination of the standard plot remained unchanged. The described method is therefore highly reproducible and reliable for estimation of protein.

Example 7

Sensitivity of the Assay

The sensitivity of the assay was assessed by comparing it with the results produced by the Lowry method. Duplicate samples of protein solution containing 0.025–0.1 mg/ml in a volume of 0.1 ml were assayed as described in Example 6 and by the Lowry method. The results gave the plots shown in FIG. 8. It is clear from the graph that the assay performed according to the described method is more sensitive than the Lowry method.

Example 8

Elimination of Interference

Figure 10:
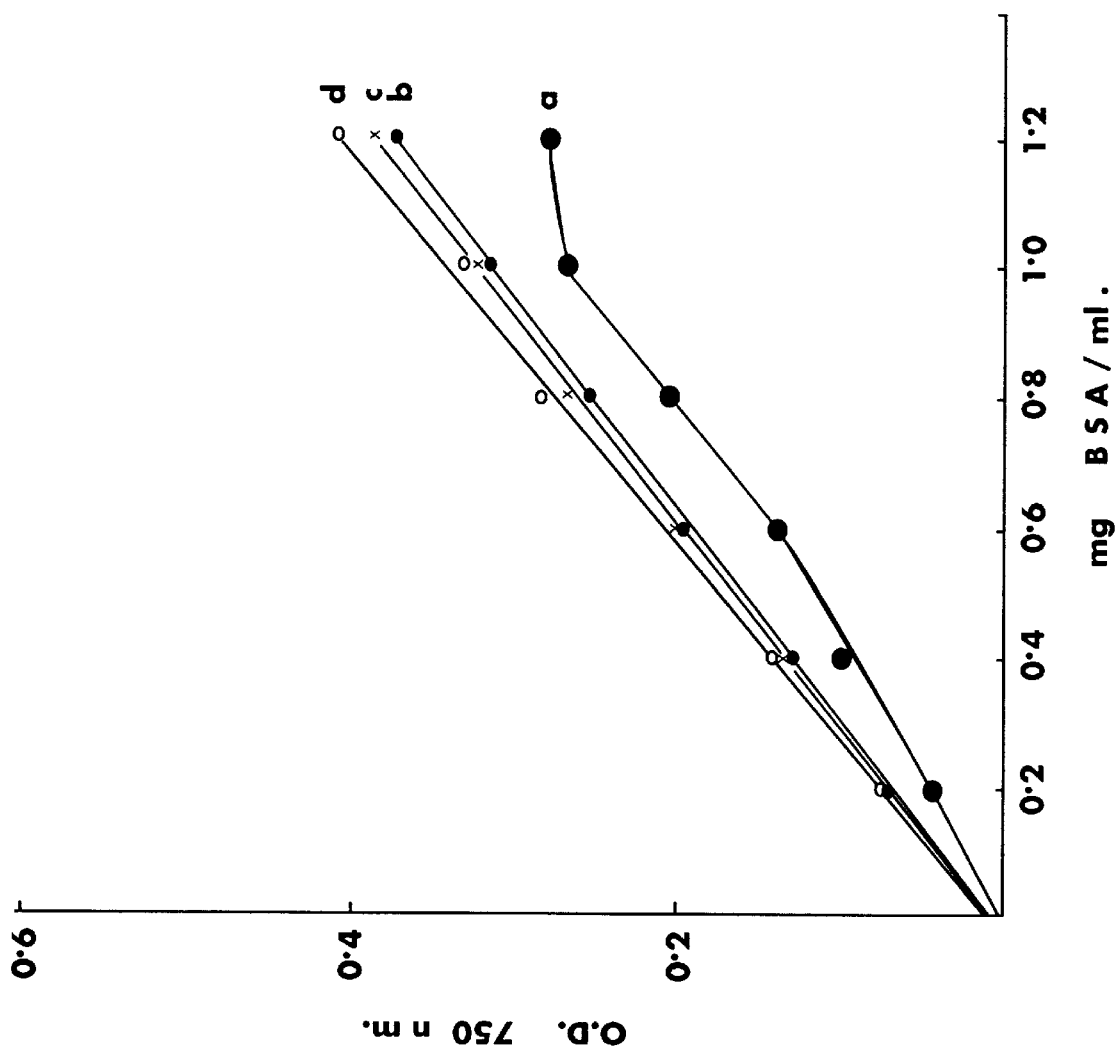

Protein assays using Folin reagent are sensitive to interference by a number of commonly used laboratory reagents. The small effects due to such agents as sucrose, EDTA, Tris and 2-mercaptoethanol can easily be eliminated by running a proper buffer control with the assay. The interference by nonionic and cationic detergents can be eliminated by introducing a small amount of the anionic detergent sodium dodecyl sulphate (SDS) (0.5%–2%) into the alkaline copper solution. Duplicate samples (0.2–1.2) were assayed as described in Example 6, except that the assays were performed with alkaline copper solution containing and lacking 2% sodium dodecyl sulphate. Protein solutions containing and lacking 1% Triton-X100 were used. The results are shown in FIG. 10. Plot B shows the control experiment, and Plot D shows the experiment in which the alkaline solution contained 2% sodium dodecyl sulphate. The addition of sodium dodecyl sulphate slightly increased the colour yield. Plot A shows protein containing 1% Triton-X100 when assayed with the reagent lacking sodium dodecyl sulphate, and Plot A was distorted because of precipitation due to the presence of Triton-X100 in the protein. Plot C shows protein of Plot A assayed with the alkaline copper solution containing 2% sodium dodecyl sulphate. It is clear from the plots that the addition of sodium dodecyl sulphate countered the influence of detergent Triton-X100 and restored Plot A. Similar results have been obtained with other nonionic and cationic detergents.

Example 9

Micro Assay System

Figure 11:
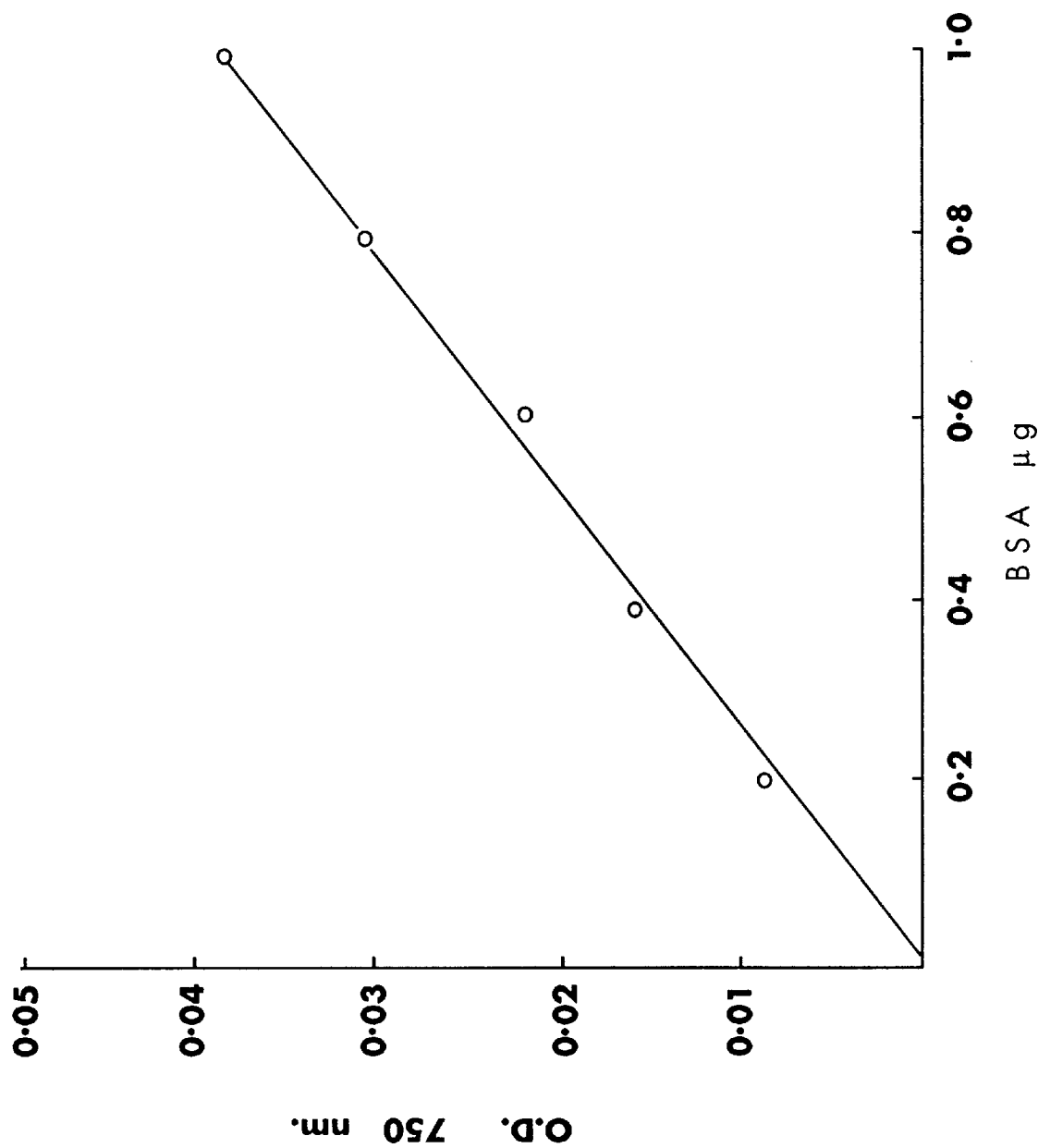

Micro protein assay was performed in either microtiter plates or micro test tubes in a total assay volume of 0.2–0.25 ml. Protein solution containing 0.2–1 $\mu$g protein in a volume of 5 $\mu$l was used. The protein samples were first treated with 25 $\mu$l of alkaline copper solution containing 1N NaOH in 5% sodium carbonate, 0.15% sodium tartrate and 0.05% copper sulphate followed by 174 $\mu$l of 5% Folin solution. The optical density was read after 10 minutes. FIG. 11 shows the results obtained for a micro assay system. It is clear from the results that the assay is capable of estimating protein at concentrations as low as 0.2 micrograms in a sample.

Example 10

Linearity of the Assay

Figure 12:
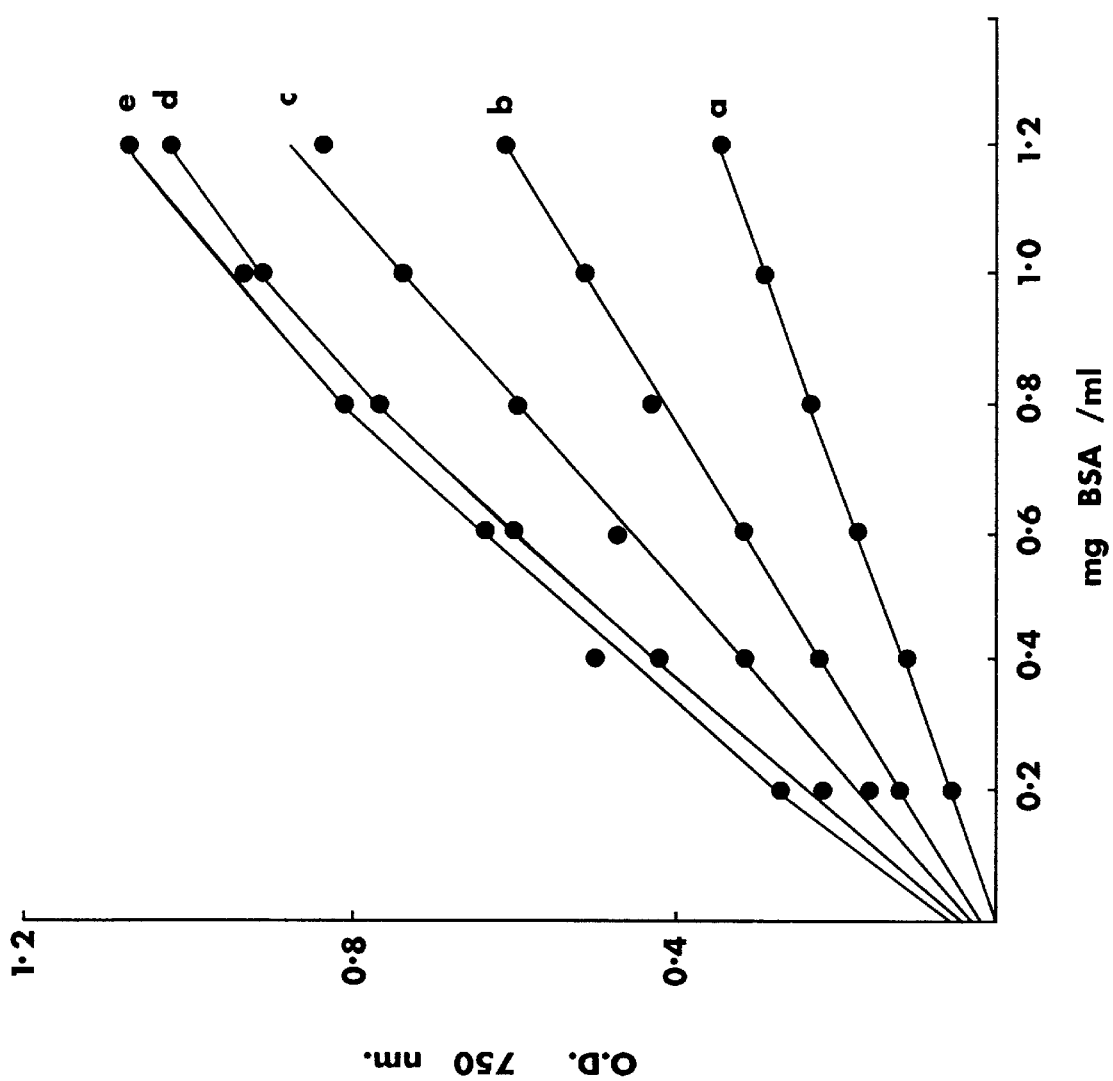

This experiment consisted of a batch of five determinations, a, b, c, d and e. Batch a contained 0.2–1.2 mg/ml protein in a total volume of 0.1 ml. Batches b, c, d and e contained 2, 3, 4 and 5 times the amount of protein present in Batch a in a total volume of 0.1 ml. The assays were performed as described in Example 6, and FIG. 12 shows the results. It is clear from the results that the assay is linear for up to 0.6–3.6 mg/ml protein per assay. Protein in excess of 0.8–4.8 mg/ml begins to lose linearity. However, it has been found that the linearity of the assay can be restored by increasing the amount of alkaline copper in the assay and correspondingly increasing the amount of Folin (results not shown).

Example 11

Stability of Alkaline Copper Solution

Unbuffered alkaline solution containing 1N NaOH and 0.16% tartrate was mixed with copper solution in order to prepare alkaline copper solutions. 0.5% SDS was added to some of the alkaline copper solutions. The solutions-alkaline copper solution lacking in SDS and alkaline copper solution containing 0.5% SDS—were routinely examined for signs of deterioration. It was found that alkaline copper solutions did not develop excessive precipitate and were good for use for months. However, the alkaline copper solution containing SDS did develop SDS precipitate, although the solution could still be used after shaking it gently, which created a homogeneous suspension, or after warming, which dissolved the SDS precipitate and gave a clear solution. It was also found (see Table 4) that the presence of a high concentration of tartrate further improved the stability of an alkaline copper solution. In the absence of tartrate, the copper precipitated out of the alkaline solution as a black precipitate.

TABLE 4

The effect of concentration of sodium/potassium tartrate on the stability of an alkaline copper solution. The alkaline copper solution contained 0.05% copper in 1N NaOH solution. The reagents were stored at room temperature over 6 months.

| Concentration Na/K tartrate in alkaline copper solution (%) | Concentration of tartrate relative to copper | Remarks of & Results |
|---|---|---|
| 0 | 0 | Black precipitate developed within hours |
| 0.16 | ×3.2 | Black precipitate developed within weeks |
| 0.26 | ×5.2 | Black precipitate in some samples |
| 0.66 | ×13.2 | All samples clear. No precipitation observed. |

I claim:

1. A kit for use in assaying protein, the kit consisting essentially of:
   (a) a pre-mixed sodium hydroxide and copper solution containing a tartrate higher than 0.16%;
   (b) a solution of Folin phenol reagent.

2. A kit according to claim 1, wherein the concentration of sodium hydroxide in the premixed alkaline copper solution is at least 0.2N.

3. A kit according to claim 2, wherein the concentration of alkali in the pre-mixed sodium hydroxide and copper solution is between 0.4 and 1N.

4. A kit according to claim 1, wherein the concentration of Folin phenol reagent in the solution of Folin phenol reagent is between 0.5N and 0.05N.

5. A kit according to claim 4, wherein the concentration of Folin phenol reagent in the solution of Folin phenol reagent is 0.1N.

6. A kit according to claim 1, wherein the tartrate in the pre-mixed sodium hydroxide and copper solution is sodium or potassium tartrate.

7. A kit according to claim 1, wherein the concentration of the tartrate is between 0.26% and 0.66%.

8. A kit according to claim 7, wherein the concentration of the tartrate is 0.66%.

9. A kit according to claim 1, wherein the weight per volume concentration of the tartrate in the pre-mixed sodium hydroxide and copper solution is higher than 3.2 times that of the copper in the solution.

10. A kit according to claim 9, wherein the weight per volume concentration of the tartrate is between 5.2 and 13.2 times that of the copper in the solution.

11. A kit for use in assaying protein, the kit consisting essentially of:
    (a) a pre-mixed sodium hydroxide and copper solution containing a tartrate higher than 0.16%, the alkaline copper solution being free from buffer; and
    (b) a solution of Folin phenol reagent.

12. A kit according to claim 11, wherein the tartrate concentration being between 0.26% and 0.66%.

13. A kit according to claim 12, wherein the concentration of the tartrate is 0.66%.

14. A kit for use in assaying protein, the kit consisting essentially of:
    (a) a pre-mixed sodium hydroxide and copper solution containing a tartrate, the weight per volume concentration of the tartrate being higher than 3.2 times that of the copper in the alkaline copper solution, the alkaline copper solution being free from buffer; and
    (b) a solution of Folin phenol reagent.

15. A kit according to claim 14, wherein the weight per volume concentration of the tartrate is between 5.2 and 13.2 times that of the copper in said alkaline copper solution.

16. A kit according to claim 15, wherein the weight per volume concentration of the tartrate is 13.2 times that of the copper in the said sodium hydroxide and copper solution.

* * * * *